United States Patent [19]

Teague

[11] Patent Number: 5,755,757
[45] Date of Patent: May 26, 1998

[54] APPARATUS FOR LOCALIZED NEUTRALIZATION OF POISON

[76] Inventor: Thomas Wade Teague, 3321 Vaucluse Rd., Aiken, S.C. 29801

[21] Appl. No.: 796,659

[22] Filed: Feb. 5, 1997

Related U.S. Application Data

[62] Division of Ser. No. 640,564, May 1, 1996.

[51] Int. Cl.$^6$ ........................................... A61N 1/04
[52] U.S. Cl. .................................... 607/115; 607/2
[58] Field of Search .......................... 439/125, 289, 439/675; 607/72, 115, 142, 148, 122, 2; 128/639; 600/372

[56] References Cited

U.S. PATENT DOCUMENTS

| | | |
|---|---|---|
| D. 355,491 | 2/1995 | Monea . |
| 2,292,216 | 8/1942 | Doran ........................... 439/125 |
| 3,788,329 | 1/1974 | Friedman ....................... 607/122 |
| 3,804,098 | 4/1974 | Friedman ....................... 607/122 |
| 4,422,124 | 12/1983 | Challet . |
| 4,694,840 | 9/1987 | Kairis et al. ..................... 607/72 |
| 4,848,352 | 7/1989 | Pohndorf et al. ................ 607/122 |
| 4,920,981 | 5/1990 | Dervieux ....................... 607/145 |
| 5,059,852 | 10/1991 | Meury . |
| 5,074,305 | 12/1991 | Guderian . |
| 5,235,990 | 8/1993 | Dempsey ....................... 607/145 |
| 5,279,299 | 1/1994 | Imran ............................ 607/126 |
| 5,350,416 | 9/1994 | Guderian . |
| 5,365,926 | 11/1994 | Desai ............................ 607/122 |
| 5,496,356 | 3/1996 | Hudz ............................. 607/115 |

*Primary Examiner*—William E. Kamm
*Assistant Examiner*—Kennedy J. Schaetzle
*Attorney, Agent, or Firm*—Haradway Law Firm P.A.

[57] ABSTRACT

An apparatus (10) and method are provided for neutralizing poison, acquired through venomous snake bites, insect bites and stings, or the like, within a localized wound area. The apparatus is preferably comprised of a housing (12) completely containing a voltage generator (14) and partially containing a cathode (16) electrically communicating with the voltage generator, the cathode having a tip (16a), and an electrical receiver (18) mounted to the housing. The electrical receiver has a distal portion (18c) bent so as to circumscribe a localized area around the cathode tip. By contacting the localized wound area with the cathode tip, by contacting a nearby skin surface with the distal portion of the electrical receiver, and by then actuating the voltage generator, such as by depressing a plunger (15), a high voltage is applied from the cathode tip, across a portion of the localized wound area, and to the distal portion of the electrical receiver. In this manner, voltage is applied in only a closely defined area, maximizing its capacity to neutralize the poison in that area.

2 Claims, 4 Drawing Sheets

APPARATUS FOR LOCALIZED NEUTRALIZATION OF POISON

This application is a division of application Ser. No. 08/640,564, filed on May 1, 1996.

BACKGROUND OF THE INVENTION

This invention relates to the treatment of venomous snake bites, insect bites and stings, or the like.

The victim of a venomous bite or sting must frequently treat the affected area immediately to prevent harmful consequences, which may include death. Even insect bites not posing an immediate threat of loss of life or limb can still be a source of significant pain or irritation for the victim. Since the availability of chemical serums to treat such conditions is not uniformly available in all geographical areas, it has become desirable to provide alternative, preferably portable, means of treatment.

The use of electrical current to treat toxic bites or stings is known. For instance, U.S. Pat. No. 5,350,416 teaches the use of an electrical probe in combination with a grounding plate. The probe is positioned at or proximate the site of the toxic bite, at one side of the affected limb, and the grounding plate is placed at the opposed side of the limb. An electrical circuit communicating with the probe applies voltage from the probe, through the limb, and to the grounding plate. While this device may suitably neutralize toxins in certain instances, the requirement that the voltage be applied through an affected limb, rather than across a localized wound area, limits the size of the portions of the wound which are affected by a single application of voltage. Hence, a significant number of applications of voltage across the body or limb may be necessary to effectively treat the wound site. Furthermore, the separateness of the discrete circuit, probe, and grounding plate acts as a limit on the portability of the device, which may not be able to be S carried in a pocket of a potential victim.

Accordingly, there is a need in the art for a readily portable apparatus for neutralizing poisons which applies voltage directly across a localized wound area.

SUMMARY OF THE INVENTION

It is thus an object of the present invention to provide a method and apparatus for localized neutralization of poison which overcome the foregoing prior art limitations.

It is a further object of the present invention to provide an apparatus for localized neutralization of poison which applies voltage across only a localized wound area.

It is a further object of the present invention to provide an apparatus for localized neutralization of poison which is pocket-sized to enhance portability.

It is a still further and more particular object of the present invention to provide an apparatus which neutralizes poison in a localized wound area by applying a high voltage from a cathode, across the localized area, and to an electrical receiver.

It is a further object of the present invention to provide an apparatus for localized neutralization of poison which includes an electrical receiver having a distal portion which is bent so as to circumscribe an area around the tip of a cathode.

These and other objects are accomplished by an apparatus for neutralizing poison in a localized wound area, comprising a voltage generator, a cathode electrically communicating with the voltage generator, the cathode having a tip, a housing partially encasing the cathode, and an electrical receiver mounted to the housing, the electrical receiver having a distal portion bent so as to circumscribe an area around the tip of the cathode. The voltage generated is thereby applied from the tip of the cathode, across a localized wound area, and to the distal portion of the electrical receiver. The application of voltage is therefore substantially limited to the wound site.

The foregoing objects are also accomplished by a method of neutralizing poison in a localized wound area, comprising the steps of providing a voltage generator, providing a cathode in electrical communication with the voltage generator, the cathode having a tip, contacting a skin surface at a wound site with the tip of the cathode, contacting the skin surface with an electrical receiver in close proximity to the tip of the cathode, and actuating the voltage generator.

DETAILED DESCRIPTION OF THE PREFERRED EMBODIMENT

Figure 1:
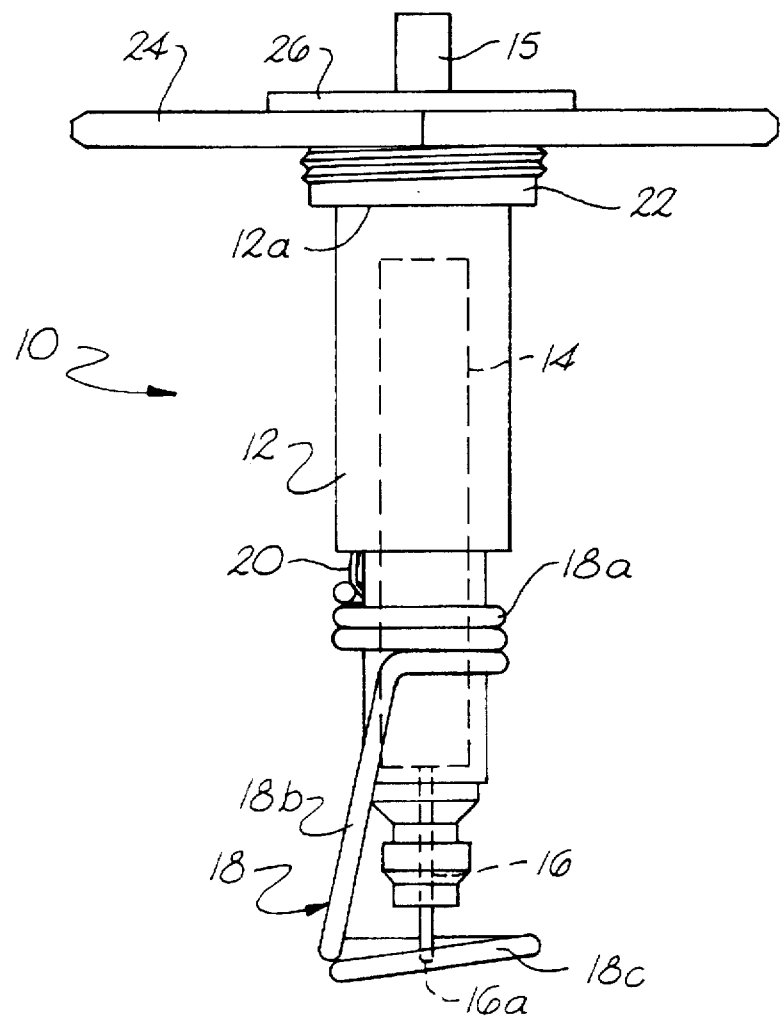
FIG. 1 is a front view of a poison neutralization apparatus constructed in accordance with a preferred embodiment of the present invention.

Referring to FIG. 1, an apparatus 10 is shown for neutralizing poison in a localized wound area. In the preferred embodiment, apparatus 10 is comprised of a housing 12 which completely encases a voltage generator 14, shown schematically in phantom lines. Voltage generator 14 preferably comprises conventional internal elements of a piezoelectric lighter, such elements being disclosed in U.S. Pat. No. 4,422,124 to Challet and in U.S. Pat. No. 5,059,852 to Meury, the disclosures of which are hereby incorporated by reference. Thus, depressing a spring-loaded plunger, such as at 15, causes the voltage generator 14 to produce a high voltage potential, preferably in the range of 15–30 kV. While piezoelectric elements are preferred, other means for production of such voltage are contemplated as being within the scope of the present invention. Apparatus 10 also includes a cathode 16 electrically communicating with the voltage generator 14, the cathode 16 having a tip 16a. Cathode 16, which may be constructed of any metal having desirable current conductivity characteristics, is shown as being partially encased by the housing 12, but protruding downwardly out of the housing 12 so that tip 16a is clearly exposed.

A metallic electrical receiver 18 is mounted to the housing 12 and includes a proximal portion 18a forming a coil which wraps around the housing 12, a medial portion 18b extending downwardly from the coil-like proximal portion 18a, and a distal portion 18c extending from the medial portion 18b. The distal portion 18c is bent so as to circumscribe an area around the cathode tip 16a, as will be more clearly seen with regard to FIGS. 3 & 4. In the embodiment shown in FIG. 1, retention of the electrical receiver 18 on the housing 12 is aided by an outwardly-biased leaf spring element 20, shown extending from the housing 12 and abutting against an end of the proximal portion 18a.

Figure 2:
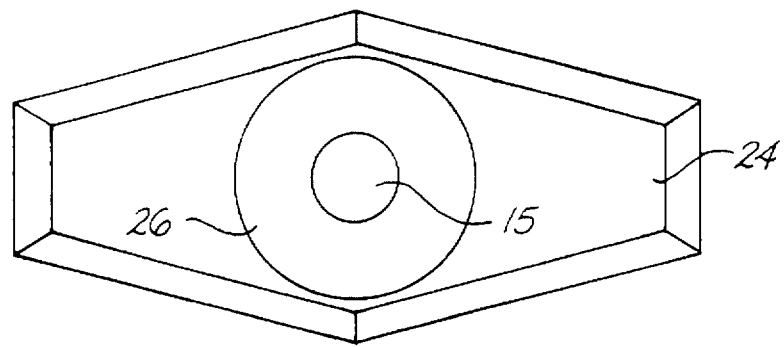
FIG. 2 is a plan view of the poison neutralization apparatus constructed in accordance with the preferred embodiment of the present invention.

Referring to FIGS. 1 & 2, apparatus 10 preferably includes additional elements to aid the user in properly grasping it. Specifically, an externally-threaded cap 22 is press fit over the upper end 12a of housing 12. A grasping plate 24 threadably engages the cap 22, and it may be held in place by means of a flange 26. Thus, a user may hold apparatus 10 by contacting the underside of grasping plate 24 with the fingerprint sides of the index finger and the middle finger, whereby the thumb can press downwardly on the plunger 15 to steady the plate 24 against those fingers. Increased pressure on plunger 15 actuates the voltage generator 14, as will be explained with regard to FIG. 4. Preferably, the housing 12, the plunger 15, the cap 22, the rasping plate 24, and the flange 26 are all constructed of a plastic material to facilitate ease in assembly.

Figure 3:
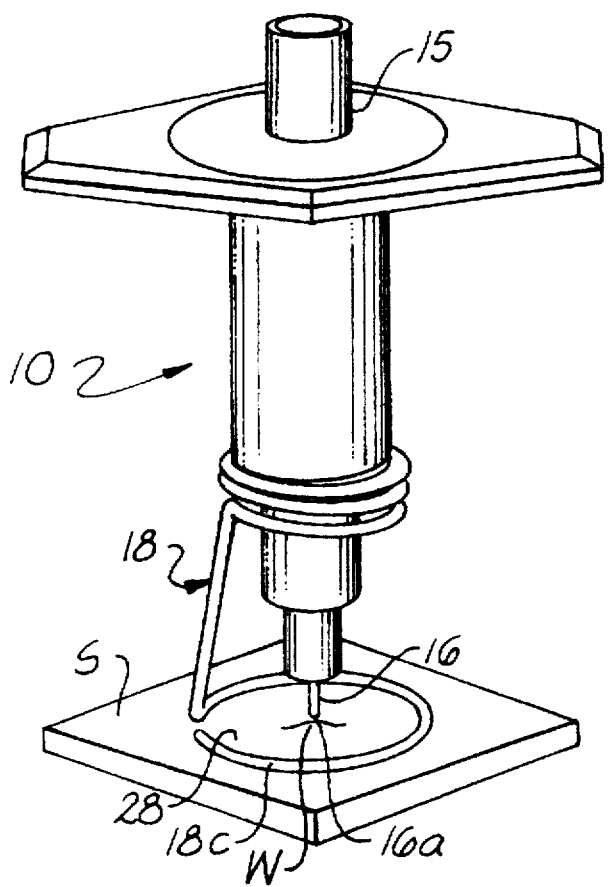
FIG. 3 is a perspective view illustrating the poison neutralization apparatus constructed in accordance with the preferred embodiment of the present invention, shown positioned with respect to a wound, preparatory to actuation of a voltage generator of the apparatus.
Figure 4:
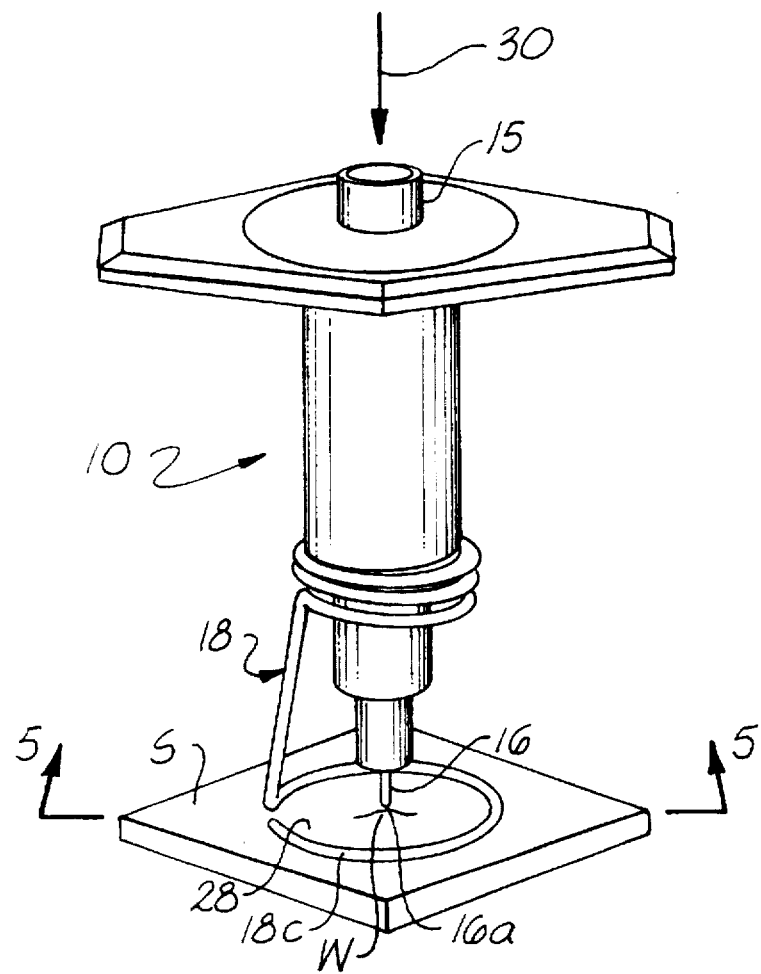
FIG. 4 is a perspective view similar to FIG. 3, except that it shows actuation of the voltage generator of the apparatus.

Referring to FIGS. 3 & 4, the intended operation of the apparatus of the present invention is shown.

In FIG. 3, apparatus 10 is shown being held just above a skin surface S which has been affected by a venomous snake or insect bite, the affected location being shown at raised wound W. Distal portion 18c of electrical receiver 18 is seen to be bent in a substantially circular shape, such that it circumscribes a circular area 28 about cathode tip 16a, with the tip 16a being in substantially the center of the defined area 28. Although shown as assuming a substantially circular shape, distal portion 18c may be bent in any suitable geometric shape, so long as cathode tip 16a is in substantially the center of the defined area 28.

Such an arrangement allows the generated voltage to be applied radially from the cathode tip 16a to any point on the distal portion 18c which, when circular, allows for almost a 360° circumferential variation of electrical receiving points. Thus, the term "localized wound area" is defined as that portion of skin surface S which is contained in area 28 when tip 16a contacts wound W, and this term includes the portion of the victim's flesh which is directly beneath the defined skin surface portion. As shown in FIG. 3, the plunger 15 is shown in its raised position, so the voltage generator 14 (FIG. 1) has not yet been actuated.

In FIG. 4, apparatus 10 is shown as being positioned such that the wound W is within area 28 and such that wound W is contacted by the cathode tip 16a. Skin surface S is contacted by the circular distal portion 18c of the electrical receiver 18. In this manner, the electrical receiver 18 is placed in close proximity to the cathode tip 16a. As it relates specifically to the preferred embodiment, the term "close proximity" is defined to mean approximately 1 cm, since that is the radial distance from cathode tip 16a to a point along distal portion 18c. However, the radial distance may vary in proportion to increases or decreases in the overall size of apparatus 10, or to the size of the affected skin area, or to particular constructions of other embodiments of the present invention, and such variations are contemplated as being within the scope of the present invention. The plunger 15 is shown as having been pressed downwardly in the direction of arrow 30, thereby actuating voltage generator 14 (FIG. 1) to produce a high voltage. Thus, the electrical voltage is applied from the cathode tip 16a, across a localized wound area, and to the distal portion 18c of the electrical receiver 18.

Figure 5:
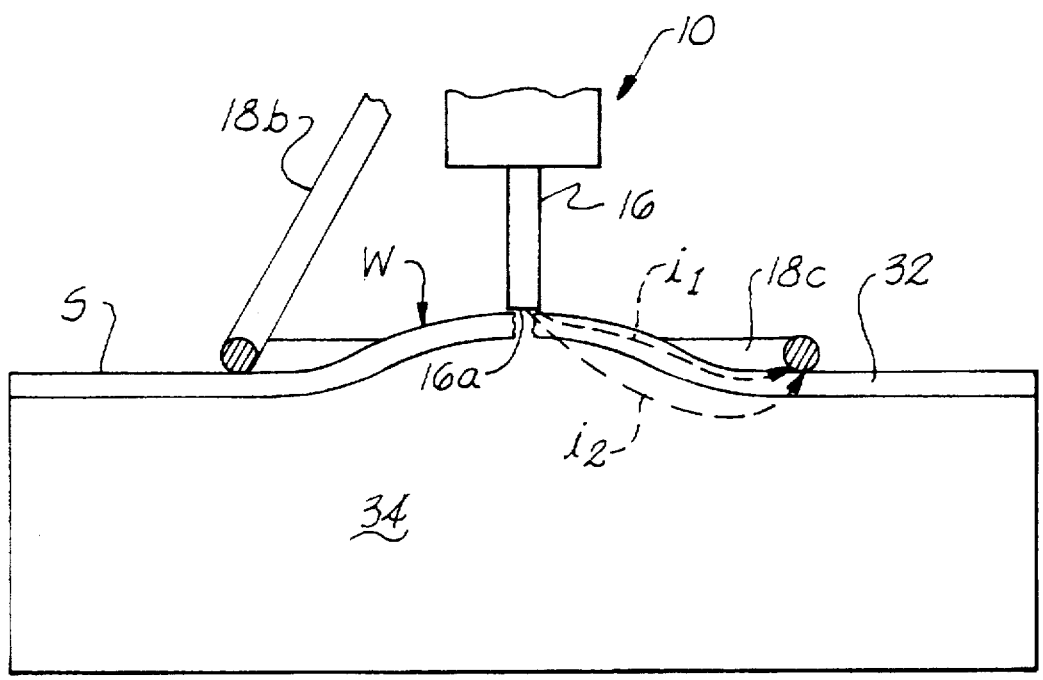
FIG. 5 is an enlarged sectional elevation view taken along line 5—5 in FIG. 4

FIG. 5 depicts the treatment of the wound W in greater detail. Cathode tip 16a is shown as contacting wound W at the point where skin 32 has been broken. At the instant voltage is applied by the apparatus 10, current travels from the cathode tip 16a to a point on the distal portion 18c of electrical receiver 18. This current branches into two separate paths. A first current path $i_1$ runs along the skin 32, and a second current path $i_2$ runs downwardly through the skin 32, into flesh portion 34 beneath the skin 32, then upwardly through the skin 32 before arriving at distal portion 18c. The magnitude of the current represented by $i_1$ and $i_2$ is small, on the order of 15–30 μA. It is therefore seen that the current produced by the apparatus 10 does not travel entirely through a limb or other body portion, but rather travels where it is most needed, namely, across and into the wound W itself.

It has been found that the overall effectiveness and speed of neutralization by apparatus 10 increases as the cathode 16 and electrical receiver 18 are placed closer to the site of poison injection into the skin. It is noted that for more poisonous bites and stings, repeated application of voltage may be necessary, depending on the magnitude of the voltage generated in one application.

Voltage is therefore applied across a short distance, from the specific point of injury to a nearby portion of skin, to neutralize the poison in the wound area. This distinguishes the present invention over prior art devices, in which the generated voltage is applied entirely across the victim's body, or entirely through a limb, rather than across only a localized wound area.

As the above description is merely exemplary in nature, being merely illustrative of the invention, many variations will become apparent to those of skill in the art. Such variations, however, are included within the spirit and scope of this invention as defined by the following appended claims.

That which is claimed:

1. An apparatus for neutralizing poison in a localized wound area, comprising:

a voltage generator;

a cathode electrically communicating with said voltage generator, said cathode having a tip;

a housing partially encasing said cathode; and an electrical receiver mounted to said housing, said electrical receiver having a proximal portion forming a coil wrapping around said housing.

2. An apparatus for neutralizing poison in a localized wound area, comprising:

a voltage generator;

a cathode electrically communicating with said voltage generator, said cathode having a tip;

a housing partially encasing said cathode; and an electrical receiver mounted to said housing, said electrical receiver having a proximal portion forming a coil wrapping around said housing;

said apparatus further comprising:

a cap seated on said housing;

a grasping plate receiving on said cap; and a flange retaining said grasping on said cap.

* * * * *